United States Patent [19]

Zuiderveld et al.

[11] Patent Number: 4,870,692
[45] Date of Patent: Sep. 26, 1989

[54] DEVICE FOR AND METHOD OF SUBTRACTION IMAGING WITH REDUCTION OF MOTION ARTEFACTS

[75] Inventors: Karel J. Zuiderveld, Nieuwegein; Ter H. B. M. Romeny, Utrecht, both of Netherlands

[73] Assignee: U.S. Philips Corporation, New York, N.Y.

[21] Appl. No.: 126,641

[22] Filed: Nov. 30, 1987

[30] Foreign Application Priority Data

Dec. 1, 1986 [NL] Netherlands ............... 8603059

[51] Int. Cl.$^4$ ............... G06K 9/00; G06K 9/32
[52] U.S. Cl. ............... 382/6; 382/44; 358/111; 364/413.23
[58] Field of Search ............... 382/6, 44; 358/111; 364/414

[56] References Cited

U.S. PATENT DOCUMENTS

| | | | |
|---|---|---|---|
| 4,558,462 | 12/1985 | Horiba et al. | 382/43 |
| 4,626,991 | 12/1986 | Crawford et al. | 364/414 |
| 4,635,293 | 1/1987 | Watanabe | 382/6 |
| 4,636,953 | 1/1987 | Kageyama | 358/111 |
| 4,641,352 | 2/1987 | Fenster et al. | 382/6 |
| 4,644,582 | 2/1987 | Morishita et al. | 382/44 |

Primary Examiner—Leo H. Boudreau
Assistant Examiner—Donald J. Daley
Attorney, Agent, or Firm—Jack E. Haken

[57] ABSTRACT

Images formed by digital subtraction angiography are improved by subtracting a locally deformed image from another image. A subtraction image is obtained which is substantially free from motion artefacts and which contains only the information of a moving contrast medium. To achieve this, a shift vector is determined for various pixels and a reliability criterion is calculated for each direction component of said shift vector.

26 Claims, 2 Drawing Sheets

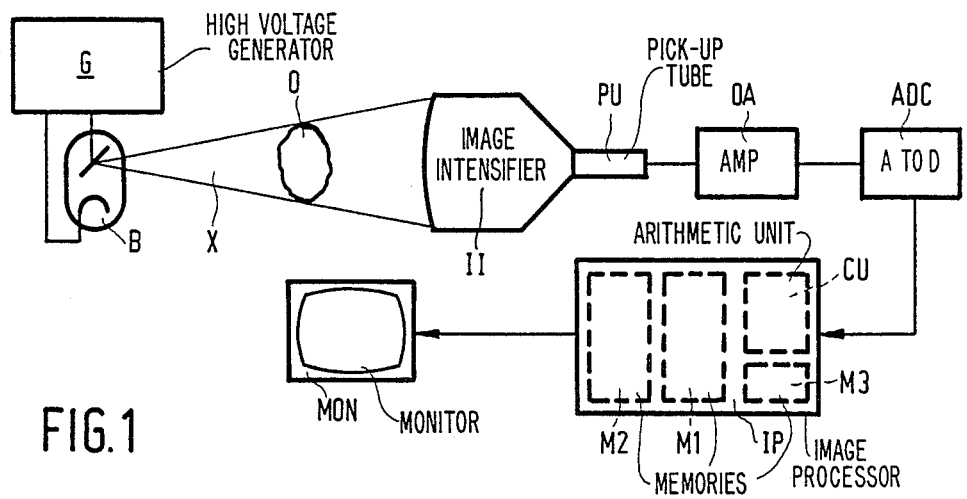
FIG.1
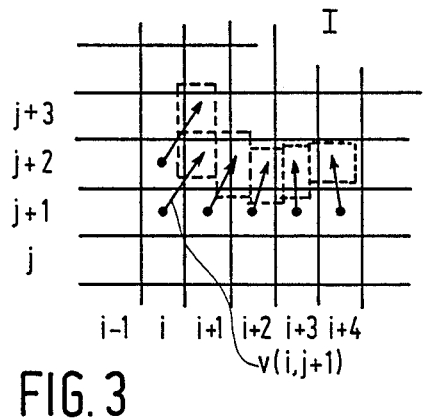
FIG.3
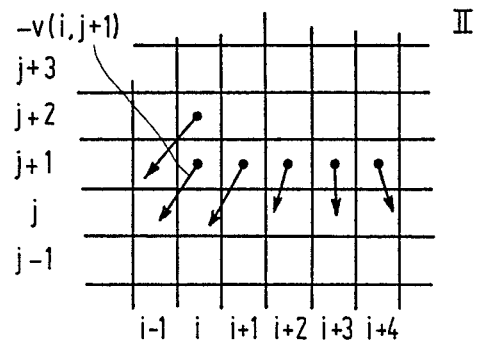
FIG.4
| | L-k | L | L+k |
|---|---|---|---|
| K+k | | 0,2 | |
| K | 0,6 | 0,4 | 0,3 |
| K-k | | 0,7 | |
FIG.5a
| | L-k | L | L+k |
|---|---|---|---|
| K+k | | 1,8 | |
| K | 0,6 | 1,4 | 1,6 |
| K-k | | 0,4 | |
FIG.5b

DEVICE FOR AND METHOD OF SUBTRACTION IMAGING WITH REDUCTION OF MOTION ARTEFACTS

The invention relates to a device for determining a subtraction image from a first and a second image, comprising:

(a) storage means for storing the first and the second image, (b) arithmetic means for selecting a sub-image, subdivided into pixels, from within the first and the second image, for shifting one sub-image with respect to the other sub-image, for comparing the values of the corresponding pixels of the two sub-images, and for determining therefrom a correspondence value and a shift vector of the shifted sub-image for which said correspondence value is maximum, said shift vector having two or more othogonal components, (c) further storage means for storing the shift vector determined, which arithmetic means are also suitable for determining shift vectors associated with different pixels in order to correct the positions of pixels of the first image by means of the locally determined shift vectors, and for determining a subtraction image from the corrected first image and the second image.

The invention also relates to a method of determining a subtraction image from two successively formed images of an object, a sub-image being selected from each of the two images subdivided into pixels, each sub-image containing the same pixels and being compared with one another each time after having been shifted with respect to one another, per sub-image there being determined a measure of the difference between pixel values of the pixels after each shift and also a shift vector, containing orthogonal direction components, for which the measure of the difference is smallest, after which the positions of pixels in an image are corrected by means of the locally determined shift vectors, for the determination of the measure of the difference the value of each pixel of one of the sub-images being increased or decreased by an amount if the sum of position indices of the pixel is even or odd, respectively, after which a subtraction sub-image is determined and the number of sign changes between the adjacent pixels in the subtraction image is counted, and in a position where the counted number of sign changes exceeds a predetermined fraction of the maximum number of feasible sign changes the measure of the difference is deemed to be the smallest.

A method and device of this kind are known from U.S. Pat. No. 4,558,462. The known device and method are used for so-termed digital subtraction angiography. Therein, a contrast medium is injected into a patient so that the subtraction image calculated from X-ray images formed before as well as after the injection of the contrast medium should show only the contrast medium. However, due to patient motions between the various X-ray exposures, for example, cardiac or respiratory motions, the structures which are assumed to be stationary, for example the ribs of the patient, will be depicted in the subtraction image as pseudo-contours of the structures in motion. It will be apparent that these additional structures are undesirable. U.S. Pat. No. 4,558,462 discloses a method of correcting such subtraction images for patient motions. Therein, the comparison of the corresponding pixels of the two sub-images is performed by means of a cross-correlation calculation. Therefrom, for each sub-image a shift of the imaged part of a patient caused by motion is determined. By correcting one image for these shifts, the number of artefacts in the subtraction image is reduced. However, it has been found that the reliability of the shift vectors thus determined is not satisfactory in many cases. Therefore, part of the motion artefact will be more or less corrected, but another part will persist. It will be apparent that this is undesirable.

It is an object of the invention to provide a device and a method in which steps are taken in order to increase the reliability of the shift vectors determined, so that a correction for motion performed by means of the shift vectors is more reliable.

To achieve this, the device in accordance with the invention is characterized in that for each shift vector the further storage means comprise several storage locations for the storage of its position, direction components and a reliability criterion for each direction component.

The reliability criteria provide an insight as regards the reliability of the shift vectors. Thus, it can be determined whether the shifts found are adequate for realizing the desired correction of the motion artefacts. Unreliable shift vectors or components thereof can be completely or partly replaced by data of neighbouring, more reliable shift vectors.

From IEEE Transactions on Medical Imaging Vol MI-3, No. 4, pp. 179–186 a method is also known for the correction of subtraction images for patient motions. The extent of the motion is obtained therein by comparing the two images after superposition of an artificial pattern on one of the images by shifting these images with respect to one another, after which the sign changes between pixels of the subtraction image are counted. Therefrom a shift of the part of a patient imaged due to the motion is determined. This method is particularly suitable for use in a device in accordance with the invention, because this method enables very simple determination of reliability criteria.

A prefered embodiment of the device in accordance with the invention in which the arithmetic means for determining the correspondence value are adapted to increase or decrease each pixel value of at least one sub-image by an amount if the sum of the position indices of the relevant pixel is even or odd, respectively, to determine a difference between corresponding pixels in the two sub-images, and to determine the number of sign changes of the differences in the successive pixels, is characterized in that the arithmetic means are adapted to determine for each orthogonal component of a shift vector three numbers of sign changes associated with the positions after the last three shifts of the one sub-image with respect to the other sub-image in the direction of the component in order to calculate a reliability number from the differences between the largest number on the one hand and the other two numbers on the other hand.

A further embodiment of a device in accordance with the invention is characterized in that the arithmetic means are adapted to compare direction components of neighbouring shift vectors and to increase a reliability criterion based on a reliability number associated with a first direction component by an amount if the first direction component deviates by less than an adjustable measure from the neighbouring direction component.

A preferred embodiment of the device in accordance with the invention is characterized in that the arithmetic means are adapted to determine a sum of direction components weighted with reliability criteria, which direction components include a direction component to be replaced as well as its direct neighbours, the arithmetic means involving in the sum to be determined only those neighbours whose reliability criterion exceeds that of the direction component to be replaced, said sum being stored in the further storage means in order to replace a direction component thus far stored in the further storage means. When the various vector components are weighted in this manner, unreliable vector information is replaced by more reliable information in a manner which is not too drastic. It has been found that after two iterations or two weighting operations a sufficiently high vector reliability is obtained for suitably approximating the place-dependent motion.

A method in accordance with the invention is characterized in that the numbers of sign changes associated with at least the last three positions of the one sub-image with respect to the other sub-image are stored, after which a reliability number is determined from the differences between the numbers, for each orthogonal component of the shift vector there being stored three numbers associated with the last three positions in each direction and a reliability number being formed for each direction component.

A method in accordance with the invention can be accelerated if, after the determination of a shift vector, the shift vector is used as the starting quantity for the determination of a neighbouring vector. Assuming that a motion of a part of a body will not exhibit a discontinuity with respect to the motion of surrounding parts of the body, the neighbouring shift vectors will deviate only little. Therefore, a previously determined shift vector is attractively used as a starting quantity for determining a next neighbouring vector, so that a position in which the sub-images deviate the least can be found in a limited number of search steps.

The invention will be described in detail hereinafter with reference to the drawing; therein:

FIG. 1 shows an embodiment of a device in accordance with the invention,

FIG. 3 shows a position correction of various pixels

FIG. 4 shows a position correction of various pixels by means of backprojection, and FIGS. 5a and b show parts of a shift vector matrix and an associated reliability criteria matrix.

Figure 2:
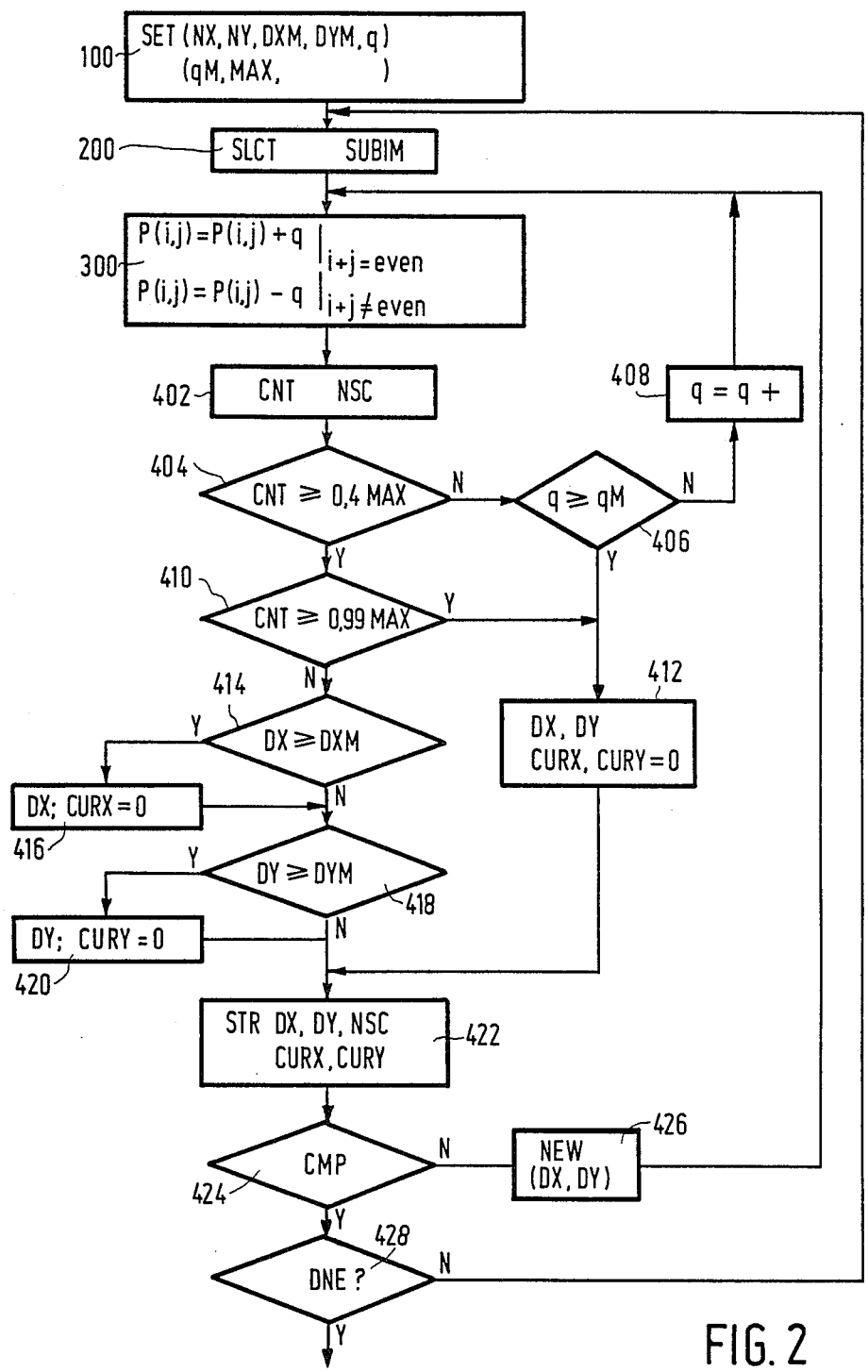
FIG. 2 shows a flow chart of the method in accordance with the invention.

FIG. 1 shows an embodiment of a device in accordance with the invention. The device comprises a high voltage generator G which powers an X-ray tube B for generating a beam of X-rays X whereby an object O is irradiated. The radiation X having passed the object O is detected by an image intensifier II and converted into an optical image which is converted into video signals by means of an image pick-up tube PU. After amplification by an amplifier OA, the video signals are sampled and digitized by an analog-to-digital converter ADC, after which the digital image signals are stored in a first or a second image memory M1, M2 of an image processing unit IP. The image processing unit IP not only comprises said memories M1 and M2, but also a further arithmetic means CU and further storage unit M3, the purpose of which will be described in detail hereinafter. The arithmetic unit CU can determine a subtraction image from the images stored in the memories M1 and M2, which subtraction image can be displayed on a monitor MON or stored in one of the memories M1, M2, M3 or in an external tape of disc memory (not shown).

The images stored in the memories M1 or M2 may be conventional shadow images, low-noise images obtained by recursive filtering, slice images generated by computer tomography, or slice images calculated from magnetic resonance signals. However, successively generated images of one and the same object where the difference between the two images is formed by is the vascular system in which a contrast medium has been injected, will also contain undesirable information concerning a motion of the object after the formation of a first image. The prior art describes attempts to eliminate the effect of a motion on the subtraction image. However, the described methods do not always offer the desired reliability.

In accordance with the invention, the image processing unit IP executes a method which mitigates the described problem. Each of the images stored in the memories M1 and M2 is divided into, for example 512×512 pixels. The arithmetic means CU select a sub-image of 32×32 pixels p1(i,j) (where $0 \leq i \leq 31$ and $0 \leq j \leq 31$) in the first image, add a value q to the pixel value of each pixel p1(i,j) if i+j is even and subtract a value q from the pixel value if i+j is odd. The sub-image thus obtained is compared with a corresponding sub-image p2(i,j) (where ($0 \leq i \leq 31$, $0 \leq j \leq 31$)) from the second image. The number of sign changes between the adjacently situated pixels in the subtraction sub-image P1(i,j)-P2(i,j) is counted. If the sub-images were identical, a maximum number of sign changes would occur. When the images are not identical, the number of sign changes is lower. By shifting one sub-image with respect to the other sub-image, a position can be found in which the number of sign changes in the associated subtraction sub-image is largest, which means that in that position the differences between the two sub-images are minimum. The extent and direction of the associated shift is referred to as the shift vector; this vector is assigned to the pixel which is situated (substantially) at the centre of the sub-image (for example, to P1(i,j), where i=j=16).

Subsequently, another sub-image is selected from the first and the second image (for example P1(i,j), where $32 \leq i \leq 63$ and $0 \leq j \leq 31$) and the described comparison method is repeated for the new sub-images. It is to be noted that the sub-images to be successively selected in an image may also overlap, so that more sub-images can be selected in an image (for example, a sub-image could contain the pixels P(i,j), where $16 \leq i \leq 47$ and $0 \leq j \leq 31$). For each selected sub-image a (locally dependent) shift vector is determined. When the sub-images are uniformly distributed across the image to be corrected, a matrix of shift vectors which are regularly distributed across the image to be corrected will thus be obtained, said matrix being stored in the further memory M3.

The process is illustrated by the abbreviated flow chart of FIG. 2. In a program block 300 in FIG. 2 it is indicated that the pixel value of each pixel P1(i,j) of a first sub-image is modified by the value q after a previous step 200 in which a sub-image is selected in dependence of a group of parameters input during a first step 100: for example, starting position (X0, Y0), sub-image size, number of pixels (NX, NY) of an image, the amount q, etc. In step 300 a subtraction image is determined from the selected sub-images. In a next group of steps as shown in FIG. 2, the position of the two sub-images with respect to one another in which the correspondence is best is determined. This group of arithmetic steps comprises a first step 402 in which the number of sign changes in a subtraction sub-image is counted. In a subsequent step 404, the number of counts is compared with a lower limit of a maximum number of feasible sign changes in the subtraction sub-image. If the number remains below this lower limit, which may amount to, for example 40%, it is tested during a next step 406 whether the value q whereby the selected sub-image has been modified has reached a maximum value qM. If this is not the case, the value q is increased by a fixed amount in a step 408, after which a new subtraction sub-image is determined in which this increased value of q is taken up in the given fixed pattern of addition and subtraction. This operation is followed by another count of the number of sign changes in the subtraction sub-image in the step 402. If it is determined in the step 404 that the number of counts exceeds the lower limit imposed, it is determined in a next test step 410 whether the number of counts exceeds a given upper limit. If this is the case, the two sub-images compared are substantially identical; subsequently, in a step 412 the last shift components DX and DY determined in the x-direction and the y-direction are assigned to a pixel which is situated substantially at the centre of the sub-image. Furthermore, a reliability number amounting to 0 is assigned to the respective pixel as will be explained hereinafter. If the counted number does not exceed the upper limit imposed, it is tested in a next test step 414 whether the shifted position associated with the sub-images exceeds a maximum value DXM in an x-direction. If this is the case, in a step 416 the last calculated value DX of the preceding shift vector is assigned to the respective pixel and an associated reliability number is deemed to be 0.

Subsequently to the instruction blocks 414 and 416, the instructions of a block 418 are executed in which it is tested whether a shift DY in the y-direction of the one sub-image with respect to the other sub-image has exceded a maximum shift DYM. If this is the case, in an instruction 420 the shift DY last calculated for the preceding vector is assigned to the pixel and the associated reliability number is deemed to be 0.

After execution of the instructions of the blocks 412, 418 or 420, the generated positions and associated counts of sign changes are stored in the block 422. In a next block of instructions 424, the successively generated counts associated with the various adjacently situated pixels are compared.

An example of the execution of the instructions in block 424 is given in IEEE Transactions on Medical Imaging, Vol. 4, No. 1984, on page 186, left-hand column. Therein a simple strategy is given for quickly finding the shift vector for a pixel.

If a maximum value can be indicated in the successively found numbers of sign changes (which means that the last number determined but one is larger than the last number and the last number but two), it is tested in block 428 whether a shift vector has been determined in each desired sub-image. If this is not the case, the image processing means IP will return to the step 200 in order to select a next sub-image.

If no maximum value can be indicated in the step 424, a new shift is selected (DX or DY is increased), after which the image processing means return to the step 300 in order to determine the number of sign changes for this shift of the sub-images with respect to one another. Not only the shift vector DX, DY as shown in block 422, but also the number of sign changes and the reliability numbers CURX, CURY are stored for reasons to be described hereinafter.

The determination of shift vectors which all contain two orthogonal components DX and DY has been described above. For an image there has been determined a matrix of shift vectors distributed across the image wherefrom a shift vector is determined for each pixel in an image in known manner by interpolation. Using these interpolated shift vectors, the position of each pixel in the image can be corrected.

FIG. 3 diagrammatically shows an example of such a position correction. FIG. 3 shows several shift vectors whose starting point is situated at the centre of a pixel and whose termination (the arrow head) forms the centre of the corrected position of a pixel. In practice the shift vectors will not represent a shift over exactly an integer number of pixels. This means that a pixel occupying a corrected position is situated between the original positions of two or more pixels. Furthermore, the dimensions of the corrected pixels will not be constant as is diagrammatically shown in FIG. 3. FIG. 3 shows the pixels in the columns i, i+1 up to and including i+4 and in the row j+1, together with the associated shift vectors. It is clearly shown that the corrected pixels, denoted by the broken lines, are not situated in the original pixel grid. It is also shown that the dimensions of the corrected pixels change because the terminations of the shift vectors shown are situated nearer to one another than their starting points. It follows from the foregoing that, if this corrected image is compared with the other image in order to determine a subtraction image, the corrected pixels need first be transformed in order to obtain comparable pixels. It will be apparent that the foregoing implies a comparatively cumbersome calculation effort. In order to avoid this, the following calculation is performed in accordance with the invention. Instead of using the positively directed shift vectors as shown in the first image I in FIG. 3, the negative shift vector in the second image II, as shown in FIG. 4, is used for determining the necessary pixel values. For example, in the pixel i, j+1 in FIG. 4 the vector $-V(i, j+1)$ is shown, being the negative vector $V(i, j+1)$ shown in FIG. 3. The foregoing means that the pixel value associated with the termination of the vector $V(i, j+1)$, is determined by the pixel value of the second image associated with the pixels $(i-1, j-1)$; $(i, j-1)$; $(i-1, j)$ and $(i, j)$. By executing a bilinear interpolation between the pixel values of these four pixels, the pixel value is determined for the pixel having the position indices $(i, j+1)$. By determining a new pixel value for each pixel of the image II in FIG. 4 in the described manner, pixel values are determined for the pixels corresponding to the pixels of the image I in FIG. 3 which enable immediate formation of a subtraction image.

As has been described with reference to FIG. 2, not only the correction values DX and DY, (together forming a shift vector) are stored, but also for each shift vector the number of sign changes NSC determined for the relevant shift vector plus reliability numbers CURX and CURY. The reliability numbers CURX ans CURY are a measure of the reliability of the direction components DX and DY of the shift vector. It will be apparent that, if the number of sign changes in the test 404 (see FIG. 2) has remained below the imposed lower limit of 40% of the maximum number of feasible sign changes, the reliability 0 is assigned to such a vector. The reliability number is also 0 when the number of sign changes exceeds a given upper limit; this is tested in the step 410 (see FIG. 2). In such a case the two sub-images compared contain substantially no information which is relevant for the subtraction image. The foregoing means that a shift vector thus determined, if any, contains irrelevant information for a subtraction image to be corrected, if necessary. The method and device in accordance with the invention aim to utilize only the shift vectors which are sufficiently reliable and which are of relevance for the subtraction image to be determined. Similarly, when a limit DXM, DYM is reached by the established components of the shift vectors DX, DY, the reliability number for the associated component of the shift vector is deemed to be 0, because shifts in the order of magnitude of the limit imposed are assumed not to occur.

For the relevant cases in which the reliability numbers are not deemed to be 0, the reliability numbers are determined as follows. The reliability number CURX, CURY amounts to twice the largest number of sign changes determined for an associated integer shift vector, reduced by the number of sign changes associated with the shift vector having a slightly larger component in the same direction, and also reduced by the number of sign changes associated with the shift vector having a smaller component in the same direction. This can be written as follows:

$$CURX = 2 \times NSC(DX,DY) - NSC(DX-1,DY) - NSC(DX+1,DY).$$

$$CURY = 2 \times NSC(DX,DY) - NSC(DX,DY-1) - NSC(DX,DY+1).$$

In the above formules, NSC denotes the number of sign changes determined in a subtraction sub-image. The indices DX, DY denote the shift in the x-direction and the y-direction, respectively, of one sub-image with respect to the other sub-image. The theoretical maximum value of the reliability numbers CURX and CURY amounts to twice the number of pixels of a sub-matrix; this value is not reached in practice. A larger numerical value of the reliability number means that for a given integer shift vector the sub-images suitably correspond and correspond substantially less well in the directly adjacent positions.

If a given vector deviates substantially from its neighbours, the relevant vector is likely incorrect. Therefore, the deviation with respect to the neighbours is also a feasible measure of the reliability. In accordance with the invention, a reliability criterion is calculated which is based on the reliability numbers CURX, CURY as well as on the deviation between the vectors themselves. Two situations can be distinguished, i.e. a first situation in which the reliability number CURX or CURY exceeds the number of pixels in a sub-matrix, and a second situation in which the number of pixels NPIX in the sub-matrix is larger than the reliability number CURX or CURY. In the first case use can be made of a proven reliability criterion RX=0.6+0.1×(the number of neighbouring vectors whose direction component in the x-direction deviates by less than one pixel width). In the second case use can be made of a proven reliability criterion RX=0.6×(CURX/NPIX)+0.1×(the number of neighbouring vectors whose shift component in the x-direction deviates by less than one pixel width). The same reliability criterion is determined for the components in the y-direction of the shift vectors. After calculation of the reliability criteria, for each shift vector of the matrix the starting coordinates X and Y, a component of the shift vector in the x-direction and a component in the y-direction, and also the reliability criteria RX and RY for the component DX and the component DY, respectively, of the shift vector are stored in the memory M3.

After determination of the reliability criteria for each component of each shift vector in the matrix, the components of the shift vectors having a lower reliability criterion can be improved by using information of the components of the shift vectors having a higher reliability criterion. For each component of a shift vector a new component is calculated by means of a weighted mean value, the difference in reliability with respect to the components in its immediate vicinity being used as a weighting factor. It is to be noted that the neighbouring components which have a reliability criterion which is lower than the reliability criterion of the vector component to be newly calculated are not taken into account. FIGS. 5a and 5b show some matrix elements of shift vectors. The matrix elements have the x and y coordinate values K−k, K+k, L−k, L and L+k (for example, k=32). The reliability criteria RX for the various matrix elements have been inserted in FIG. 5a. For the corresponding matrix elements the associated components DX in the x-direction have been inserted in FIG. 5b. Hereinafter an example will be described of the calculation of a new component DX' for the shift vector component DX for the pixel K, L, the vector components of the matrix elements (L, K+k) and (L+k, K) not being taken into account because the reliability criterion RX for these matrix elements is lower than the reliability criterion of the matrix element (L, K). The new component DX' of the shift vector (L, K) has the value:

$$DX' = \frac{0.4 \times 1.4 + (0.6 - 0.4) \times 0.6 + (0.7 - 0.4) \times 0.4}{0.4 + (0.6 - 0.4) + (0.7 - 0.4)} = 0.888.$$

It has been found in practice that, if a new component has been calculated for each shift vector for each matrix element in the described manner, adequate reliability will be obtained for each vector within the matrix after a second iteration. Subsequently, from the vectors thus determined a shift vector is calculated for each pixel of a first image by means of bilinear interpolation, after which, using the negative shift vector in the second image, a pixel value is calculated for the pixel corresponding to the pixel in the first image, utilizing the backprojection method described with reference to the FIGS. 3 and 4.

What is claimed is:

1. A method of determining a subtraction image from two successively formed images of an object, a sub-image being selected from each of the two images subdivided into pixels, each sub-image containing the same pixels and being compared with one another each time after having been shifted with respect to one another, for each sub-image there being determined a measure of the difference between pixel values of the pixels after each shift and also a shift vector, containing orthogonal direction components, for which the measure of the difference is smallest, after which the positions of pixels in an image are corrected by means of the locally determined shift vectors, for the determination of the measure of the difference the value of each pixel of one of the sub-images being increased or decreased by an amount if the sum of the position indices of the pixel is even or odd, respectively, after which a subtraction sub-image is determined and the number of sign changes between the adjacent pixels in the subtraction image is counted, and in a position where the counted number of sign changes exceeds a predetermined fraction of the maximum number of feasible sign changes the measure of the difference is deemed to be the smallest, characterized in that the numbers of sign changes associated with at least the last three positions of the one sub-image with respect to the other sub-image are stored, after which a reliability number is determined from the differences between the numbers, for each orthogonal component of the shift vector there being stored three numbers associated with the last three positions in each direction and a reliability number being formed for each direction component.

2. A method as claimed in claim 1, characterized in that the reliability number is determined from the differences between the largest number determined and the other two numbers.

3. A method as claimed in claim 1 or 2, characterized in that a shift vector is compared with neighbouring shift vectors, a reliability criterion based on a reliability number associated with a direction component of the former vector being increased by an amount if a direction component deviates from the direction component of the neighbouring shift vector by less than a measure which can be adjusted in advance.

4. A method as claimed in claim 1 or 2, characterized in that a direction component of a shift vector is replaced by a sum of direction components weighted by reliability criteria, which direction components include the original direction component and its direct neighbours, only those neighbours whose reliability criterion is higher than that of the direction component to be replaced making a contribution to the sum.

5. A method as claimed in claim 1, characterized in that the number of shifts in a direction is limited to a maximum value to be selected.

6. A method as claimed in claim 1, characterized in that the amount is increased if for each position the number of sign changes is below a given lower limit.

7. A method as claimed in claim 6, characterized in that the amount is step-wise increased to a given maximum value, after which, if the number of sign changes remains below the lower limit, a shift vector equal to the directly previously determined shift vector and a reliability number zero are assigned to the pixel.

8. A method as claimed in claim 1, characterized in that, after determination of a shift vector, this shift vector is used as a starting quantity for determining a neighbouring vector.

9. A method as claimed in claim 1, characterized in that a pixel value of an image to be corrected is determined by determining for the relevant pixel corrected coordinates by combining the coordinates of the relevant pixel and the inverted shift vector, after which a pixel value for the relevant pixel is determined by interpolation of pixel values associated with pixels having coordinates in the direct vicinity of the corrected coordinates.

10. A method as claimed in claim 1, characterized in that from the pixel values of the pixels corrected by means of the shift vectors pixel values are determined by interpolation for pixels in the positions of the pixels of the non-corrected image.

11. A method as claimed in claim 9 or 10, characterized in that the interpolation is a bilinear interpolation.

12. A device for determining a subtraction image from a first image and a second image, each of said images being divided into pixels which are identified by position indices, comprising:

image processing means which select pairs of sub-images, each pair consisting of a first sub-image which is selected from within the first image and a second sub-image which is selected from within the second image; which shift the first and second sub-images in each pair relative to one another; which compare values of corresponding pixels in said relatively shifted first and second sub-images of each pair of sub-images and which determine from each of said comparisons a correspondence value and a corresponding shift vector, said shift vectors each having at least two orthogonal components; and which select for each pair a maximum correspondence value and its corresponding shift vector;

means which calculate a reliability criterion value for each component of each selected shift vector;

image correcting means which locally correct the size and positions of pixels in the first image based on the reliability criterion values and as a function of a value of the shift vectors which were selected for a pair of sub-images associated with the corrected pixel.

13. The device of claim 12 further comprising means which calculate a difference between said locally corrected first image and said second image.

14. The device of claim 12 further comprising means which identify unreliable shift vector components on the basis of associated reliability criteria values and which replace said unreliable components with reliable shift vector components associated with neighboring pixels.

15. The device of claim 14 wherein the means which replace unreliable components of shift vectors replace unreliable components of a shift vector associated with a pixel with a weighted sum of values of corresponding components of selected shift vectors associated with neighboring pixels, the values of said corresponding components being weighted with their reliability criterion values.

16. The device of claim 15 wherein said means which replace unreliable components replace said components with the weighted sum of said values of neighboring components whose corresponding reliability criterion values exceed the reliability criterion value which corresponds to the replaced component.

17. The device of claim 13 further comprising means which identify unreliable shift vector components on the basis of associated reliability criteria values and which replace said unreliable components with components of reliable neighboring shift vectors.

18. The device of claim 17 wherein the means which replace unreliable components of shift vectors replace unreliable components of a shift vector associated with a pixel with a weighted sum of values of corresponding components of selected shift vectors associated with neighboring pixels, the values of said corresponding components being weighted with their reliability criterion values.

19. The device of claim 17 wherein said means which replace unreliable components replace said components with the weighted sum of said values of neighboring components whose corresponding reliability criterion values exceed the reliability criterion value which corresponds to the replaced component.

20. The device of claim 12, 13, 14, or 17 wherein the image processing means which determine the correspondence values include:
   means which increases a value of each pixel in a sub-image in each pair of sub-images by a determined amount if the sum of the position indices which identify said pixel is even and which decrease said pixel value if said sum of indices is odd;
   means means which determine a difference between corresponding pixel values in each relatively shifted pair of sub-images; and
   means which count a number of sign changes between values of successive pixel values in said difference; and
   wherein said means which calculate the reliability criterion, for each shift vector orthogonal component, determine three of said numbers of sign changes associated with three previous relative positions of the sub-images in the pair, taken in the direction of the orthogonal component, for each shift vector; and which calculate the reliability criterion for said component from the differences between said three numbers.

21. The device of claim 20 wherein the means which calculate the reliability criterion increase by a predetermined amount the value of the reliability criterion associated with a component of a shift vector associated with a pixel if the value of said component does not differ from the values of corresponding components of shift vectors associated with neighboring pixels by more than an adjustable measure value.

22. The device of claim 12 wherein the means which calculate the reliability criterion increase by a predetermined amount the value of the reliability criterion associated with a component of a shift vector associated with a pixel if the value of said component does not differ from the values of corresponding components of shift vectors associated with neighboring pixels by more than an adjustable measure value.

23. The device of claim 12 or 13 wherein the image processing means determine the shift vectors by bilinear interpolation in a matrix of shift vector values which are regularly distributed across an image.

24. The device of claim 12 or 13 further comprising an x-ray imaging system which includes an x-ray source, image pick-up means and an analog to digital converter connected to produce said first image and said second image.

25. The method of claim 1 wherein the two images are are x-ray images at least one of which depicts a contrast medium in a body.

26. The method of claim 1 wherein the two images are successively formed x-ray angiography images of the body of a patient.

* * * * *